(12) United States Patent
Naoum

(10) Patent No.: US 10,537,719 B2
(45) Date of Patent: Jan. 21, 2020

(54) DEVICE AND METHOD OF CONTROLLED PROVISION OF THERAPEUTIC LIQUID IN THE NOSE

(71) Applicant: George Naoum, Gkizi Attikis (GR)

(72) Inventor: George Naoum, Gkizi Attikis (GR)

( * ) Notice: Subject to any disclaimer, the term of this patent is extended or adjusted under 35 U.S.C. 154(b) by 0 days.

(21) Appl. No.: 15/676,776

(22) Filed: Aug. 14, 2017

(65) Prior Publication Data
US 2017/0340869 A1  Nov. 30, 2017

Related U.S. Application Data

(63) Continuation-in-part of application No. 14/780,072, filed as application No. PCT/GR2014/000020 on Mar. 24, 2014, now Pat. No. 9,730,858.

(51) Int. Cl.
| | | |
|---|---|---|
| *A61M 31/00* | (2006.01) | |
| *A61M 3/02* | (2006.01) | |
| *A61B 17/24* | (2006.01) | |

(52) U.S. Cl.
CPC .......... *A61M 31/00* (2013.01); *A61M 3/0254* (2013.01); *A61M 3/0279* (2013.01);
(Continued)

(58) Field of Classification Search
CPC ...... A61M 2205/073; A61M 2205/075; A61M 31/00
See application file for complete search history.

(56) References Cited

U.S. PATENT DOCUMENTS

| | | | |
|---|---|---|---|
| 1,856,811 A | 7/1931 | Inaki | |
| 3,874,380 A * | 4/1975 | Baum | ............... A61M 15/0028 |
| | | | 128/200.14 |

(Continued)

FOREIGN PATENT DOCUMENTS

| | | |
|---|---|---|
| CN | 201283082 Y | 8/2009 |
| EP | 2143411 A1 | 1/2010 |

(Continued)

OTHER PUBLICATIONS

Notification of Transmittal of the International Preliminary Report on Patentability for International Application No. PCT/GR2014/000020 dated Mar. 6, 2015, by the EPO, Munich, Germany.

(Continued)

*Primary Examiner* — Nilay J Shah
(74) *Attorney, Agent, or Firm* — Peter B. Scull; HDC IP Law LLP

(57) ABSTRACT

Methods and devices for providing liquids to nasal and/or paranasal cavities are disclosed. Probe portions of a first and of a second probe are introduced to a user's first and second nostril, respectively. Each probe has a primary channel and a secondary channel. Fluid is provided to the secondary channels to expand the expandable portions of the secondary channels, seal the nostril openings and expand alar sidewalls of the nostrils. This may reveal ducts that lead to the paranasal cavities. The liquid is provided through the primary channels to the nasal cavity, the liquid being disposed to reach and stimulate the soft palate, and may trigger a swallow reflex to raise the soft palate and exert pressure to the liquid, the liquid may find an escape route through the ducts and into the paranasal cavities.

12 Claims, 10 Drawing Sheets

(52) U.S. Cl.
CPC .......... *A61B 2017/246* (2013.01); *A61M 2202/0468* (2013.01); *A61M 2205/8206* (2013.01); *A61M 2210/0681* (2013.01)

(56) References Cited

U.S. PATENT DOCUMENTS

| | | | |
|---|---|---|---|
| 5,417,652 A * | 5/1995 | Scott, Sr. | A61H 35/04 604/19 |
| 5,921,233 A | 7/1999 | Gold et al. | |
| 8,298,182 B2 | 10/2012 | Abate et al. | |
| 2006/0095066 A1 * | 5/2006 | Chang | A61B 17/1204 606/199 |
| 2007/0119451 A1 * | 5/2007 | Wang | A61M 15/0028 128/203.15 |
| 2008/0047559 A1 | 2/2008 | Fiori | |
| 2011/0040250 A1 | 2/2011 | Abate et al. | |
| 2011/0087174 A1 | 4/2011 | Carpenter | |
| 2011/0301569 A1 | 12/2011 | Dyer | |
| 2012/0083516 A1 * | 4/2012 | Mansfield | A61K 31/167 514/400 |

FOREIGN PATENT DOCUMENTS

| | | |
|---|---|---|
| EP | 2389918 A1 | 11/2011 |
| FR | 2297032 A1 | 8/1976 |
| GB | 125967 A | 10/1919 |
| GB | 2395129 A | 5/2004 |
| WO | 8905163 A1 | 6/1989 |
| WO | 2003041780 A2 | 5/2003 |
| WO | WO2010056491 A2 | 5/2010 |

OTHER PUBLICATIONS

International Search Report and Written Opinion of the International Searching Authority for PCT/GR2014000020 dated Jul. 14, 2014, 9 pages, by the EPO, (International Search Report from EPO Rijswijk, NL, Written Opinion from EPO Munich, DE).

Reply to the Written Opinion of the International Searching Authority for PCT/GR2014000020 dated Jan. 26, 2015, 30 pages, by applicant.

* cited by examiner

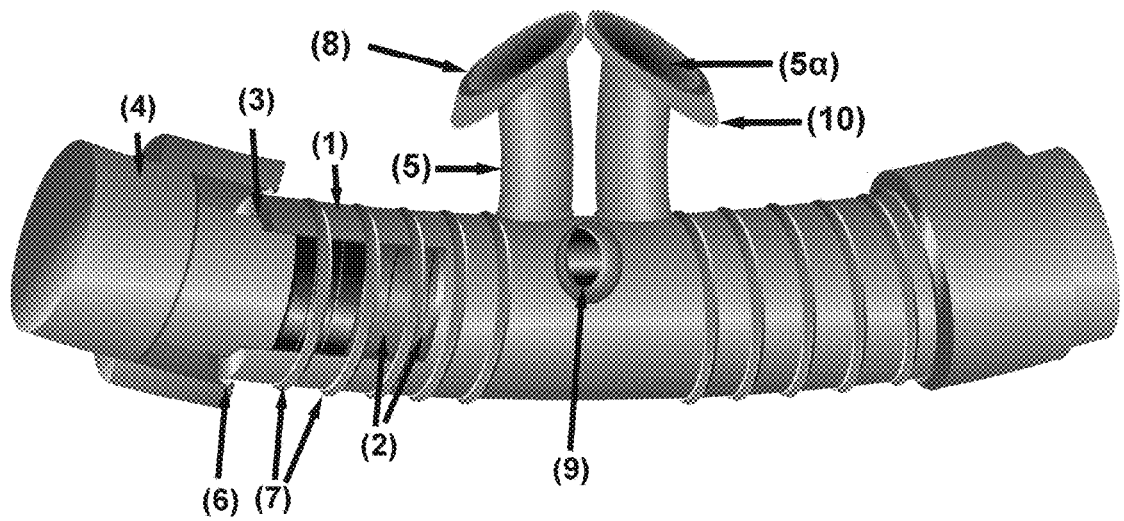
Fig. 1d
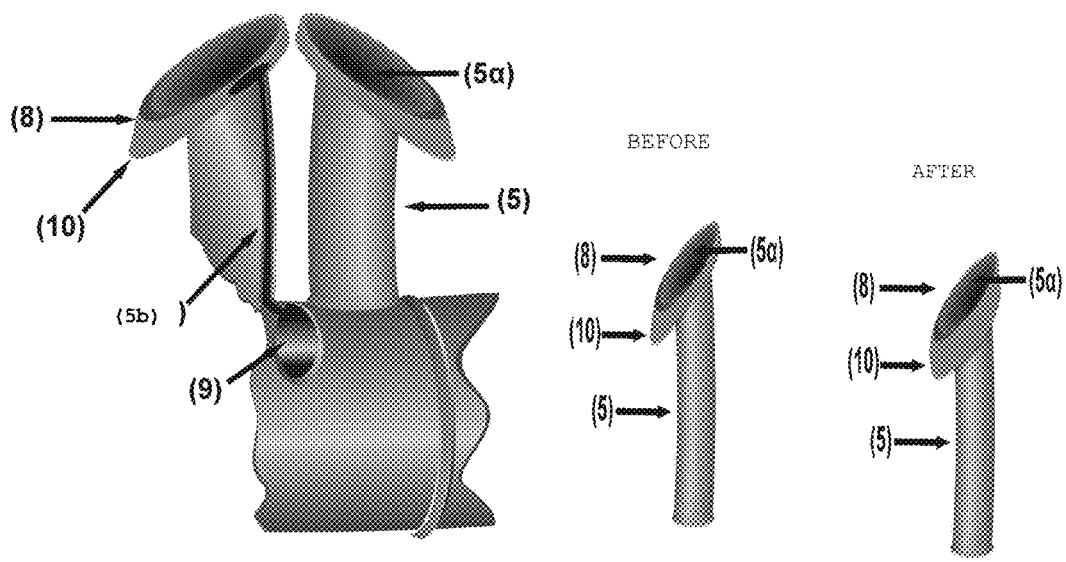
Fig. 1e
Fig. 1f

DEVICE AND METHOD OF CONTROLLED PROVISION OF THERAPEUTIC LIQUID IN THE NOSE

The developments hereof relate to devices and methods of controlled provision of a quantity of therapeutic liquid in the nasal and/or paranasal cavities and/or the nasal conchae.

These may be used for the disinfection of nasal and/or paranasal cavities, and/or the prevention of infections and/or for the treatment of chronic diseases of the upper respiratory system.

BACKGROUND

Viral infections and microbial infections of the visceroc-ranium (also called splachnocranium), i.e. of the nostrils and/or paranasal cavities, that include one or more of the maxillary sinuses (Rg), the frontal sinuses (Re), the ethmoidal sinuses or air cells (Rs), and/or the sphenoidal sinuses (Rw), form part of one of the basic health problems of humans of any age and have been major issues requiring solutions, ideas and actions from the medical community over the years.

Infections of the viscerocranium can affect one or more of a) the lower and/or upper respiratory system, b) the ears, c) the tonsils, d) children's teeth, e) sleep apnea, etc.

Researchers and medical device manufacturers, acknowledging the great benefits to humans of having a healthy respiratory system, continuously try to find ways to inject therapeutic solutions to the paranasal sinuses. Many existing devices use various techniques but only partially achieve a cleaning of the nostrils from excretions and do not succeed in injecting in a controlled manner therapeutic solutions to the paranasal sinuses.

It is also known that for the treatment of disorders of the upper respiratory and the cranium visceral sea water may be used due to its anaplastic, healing and/or hypertonic characteristics.

Proper use of sea water may relieve nasal irritation and/or restore normal function by its anti-pro-inflammatory and/or cell—regenerative characteristics, which may be superior over those of normal saline.

For an understanding of the utility of sea water in a human organism, its characteristics and its action shall be first described.

Sea water, as it is known, is a hypertonic liquid due to the increased content of NaCl (9 g/l) as well as due to the more than 80 minerals and trace elements, including calcium, magnesium, iron, copper, manganese, zinc and other elements that it contains, a composition that may give great osmotic ability and/or important nutritional and healing value.

However, other liquids, such as medicinal liquids, e.g. antibiotic solutions, for the upper respiratory system or liquids containing extracts of herbal plants may also or alternatively be beneficial for the upper respiratory and more specifically for the viscerocranium. Examples of herbal plants may include, among others, chamomile, eucalyptus, dittany of Crete or hop marjoram (*Origanum dictamnus*).

The phenomena of osmosis and/or nutritional and healing action in order to give desirable benefits may necessarily require contact of the hypertonic sea water, or other liquids as described herein, with the mucosa of the ducts or the sinuses of the nose for a sufficient period of time of stable application.

A Valsalva maneuver or exercise is a method of exhalation through the nose with closed nostrils and is applied for the handling of arrhythmias and/or for the equalization of atmospheric pressure of the tympanic membrane. Using a Valsalva exercise, pressure is applied towards the nasal canals and nasal cavities.

Currently, sea water is used for cleaning of nasal cavities with simple cleaning devices by spraying or continuous flow and may follow a direct absorption of the water. By these prior processes, the time provided can typically not be enough, as well as providing an insufficient minimum pressure of a fixed column of water and the consequent failure of impulsion of a Valsalva maneuver, which may provide for the water to enter in the nasal canals and the ducts of the nasal cavities and the osmotic phenomenon to take place, and therefore the healing result is not obtained.

This fact constitutes a vacancy in existing medical practice, worldwide, that the present developments come to fulfill. For a better understanding some elements of the physiology and pathology of the upper respiratory system shall be explained.

The respiratory system is subject to continuous risks of viral diseases and microbial infections, mainly in winter.

The respiratory system is armed with various systems of protection, one of them being the mucosa of the nasal cavities. These provide a main respiratory route and a filter of inhaled air from various suspended particulates and microorganisms.

Simultaneously the nasal cavity has a nest of prevalence of populations of viruses and microbes for a very large period throughout the entire year, mainly in winter, that are mainly the cause of development of various infections of the upper and lower respiratory system, namely of the nasal sinuses and more specifically of the supramaxillary hiatus.

These infections usually conclude to a sub-acute form with mild signs from the nasal cavity and often acquire the characteristics of chronicity and as a result they turn to new resources of microbe carriers and infections.

This phenomenon concerns all ages but mainly younger people and especially children.

By this way the nasal cavities and nasal sinuses are transformed, from protection bodies of the respiratory system, to nests of small or greater infections.

The mucosa of the nasal sinuses is subject to disorders such as edema, fattening, dryness, hyperemia, hypertrophy and obstruction of the free passage and cleaning of inhaled air.

The problem becomes even worse by the encumbrance of the environment mainly of urban centers, the dryness of air in residences (air conditioners, heating bodies etc.) that results in further decaying the mucosa, the dehydration of the excreta disposed in the surface of the endothelium and therefore obstruction of the natural air ducts, difficulty in channeling of excreta of the nasal sinuses and impedance of the free passage of air.

Structural and operational disorders of the cranium visceral in combination with the encumbrance of the mucosa of the air ducts of the oral part of the pharynx, trachea and bronchus due to encumbered environmental conditions, decrease defensive ability and form suitable ground for easier development of infections, more specifically when the organism is exposed to adverse conditions of cold, extreme fatigue, unrest, abuses etc.

So maintenance of clear and healthy nasal cavities and nasal sinuses of human beings must be part of proper medical, family and/or personal care.

Continuous systematic research of the international medical community has resulted in recommendations of hygienic living conditions and treatments, aiming for support of the immunologic ability of the organism and prevention of infections of the upper and lower respiratory system.

Nursing and care for the hygiene of the upper respiratory system and mainly of the nasal cavity and nasal sinuses targets on the one hand maintenance of a healthy mucosa and disinfection of the cavities and on the other hand on sanitation, when chronic disorder and decay exists.

For accomplishment hereof topical use may be made of various preparations among which are sea water or extracts of herbal plants.

Useful information for the benefits and the time of application of sea water may be taken for example from bathers using swimming masks for e.g. 30 to 60 minutes.

During swimming with masks the nasal bags of a mask are filled with sea water that then fills the nasal cavities of the swimmer, these nasal cavities then staying filled during the time period of swimming. The nasal bags assist in providing a hydrostatic external pressure to part of the sea water which comes to the nasal sinuses and from time to time is removed by periodic ingestion by the swimmer, and therefore the nasal cavities, the oral part of the pharynx and/or the mouth of the Eustachian channels are cleared.

During ingestion with closed nostrils as in swimming with a mask, the elevation of the soft palate for the isolation of the oral part of the pharynx from the mouth pharynx, opens the Eustachian channels and presses or pushes the water into the nasal ducts, where the excretory ducts of the nasal sinuses discharge, by forming a variation of an automated Valsalva exercise.

By the pressure enforced by the ingestion's movement of the soft palate, the water is gradually pushed inside the ducts and mainly via the sinus foramen the supramaxillary hiatus is filled.

During swimming where the nasal cavity and ducts remain full with a stable quantity of sea water under pressure, a sufficient period is offered for the hypertonic characteristic of sea water to assist in providing an osmotic phenomenon together with the assistance of movements of a Valsalva exercise the mucosa of the nasal cavities and nasal sinuses may be cleared.

After swimming it is noted that for a long lasting period often even more than an hour, a large quantity of fluid, or semi-fluid up to a high viscosity white, off white or yellow green may be aborted from the nose of the swimmer.

Such excretions may derive either from the mucosa of the nasal cavity and/or the nasal conchae and/or from the nasal and/or paranasal sinuses, which by osmosis and cleaning were removed from those cavities cleaning those ducts and the excretory ducts. By this way the relevant mucosa may be healthfully treated and/or renewed.

Exposure of nasal cavities to sea water is beneficial to the upper and to the lower respiratory system.

Driven by the above set forth herein are the developments of methods and devices that may at least partially resolve one or more of the aforementioned problems while providing benefits of therapeutic liquids to and/or in the nasal and/or paranasal cavities.

SUMMARY

The proposed methods and devices hereof may provide for cleaning the nostrils and/or may also beyond cleaning the nostrils, achieve injection of one or more therapeutic solutions to the paranasal cavities.

The filling of the paranasal cavities may be achieved with one or more of the methods hereof and/or provided by the use of the proposed devices. The methods and/or devices hereof may provoke one or the other or a combination of the reflex of swallowing and a variation of the Valsalva maneuver.

In a first aspect, a method of providing liquid to nasal and/or paranasal cavities is provided. The method may include introducing relative probe portions of a first probe and of a second probe, to a user's first and second nostrils, respectively, wherein each probe includes a primary channel and a secondary channel; providing fluid to the secondary channels to expand the probe portion of the secondary channels, seal the nostril openings and expand the alar sidewalls of the nostrils which may reveal ducts that lead to the paranasal cavities; providing a quantity of liquid through the primary channels to the nasal cavity, in some implementations, the quantity of liquid disposed to reach and stimulate the soft palate, and in some implementations to trigger a swallow reflex that raises the soft palate and exerts pressure to the liquid, whereby the liquid finds an escape route through the ducts and into the paranasal cavities.

The user's head may be in an inclined (bent forward) position during the application so that the soft palate can be triggered before any liquid reaches the pharynx.

In another aspect, a device is set forth herein which may provide, in a controllable and/or repeatable manner, a quantity of liquid into the nasal and/or paranasal cavities through both nostrils of a nose. The device may include a primary dispenser for dispensing intranasal liquid, a secondary dispenser for dispensing fluid and a first and a second probe, each probe including a portion to be fitted to the respective nostril of the nose. Each probe may include a primary and a secondary channel. Each primary channel may be attached to the primary dispenser. Each secondary channel may include an expandable and closed portion on one side to be fitted to the respective nostril and may be attached to the secondary dispenser on the other side. The fluid secondary dispenser may be configured to provide a quantity of fluid to the expandable portion of the secondary channels to expand the expandable portions in the nostrils, to seal the nostrils, push the alar sidewalls of the nostrils outwards and in some implementations reveal ducts leading to the paranasal sinuses. The primary dispenser may be configured to provide the quantity of intranasal liquid to the primary channels upon actuation of the primary dispenser after the secondary channels have sealed the nostrils. Upon provision of the quantity of liquid, the soft palate may be stimulated by the intranasal liquid and the swallowing reflex may be triggered that may cause the soft palate to move upwards and exert pressure to a surface of the intranasal liquid and may cause a portion of the intranasal liquid to penetrate the ducts leading to the paranasal cavities.

BRIEF DESCRIPTION OF THE DRAWINGS

Non-limiting examples of the present disclosure will be described in the following, with reference to the appended drawings, in which:

FIGS. 1d, 1e and 1f show a non-limiting example of a device hereof;

DETAILED DESCRIPTION OF EXAMPLES

Figure 1A:
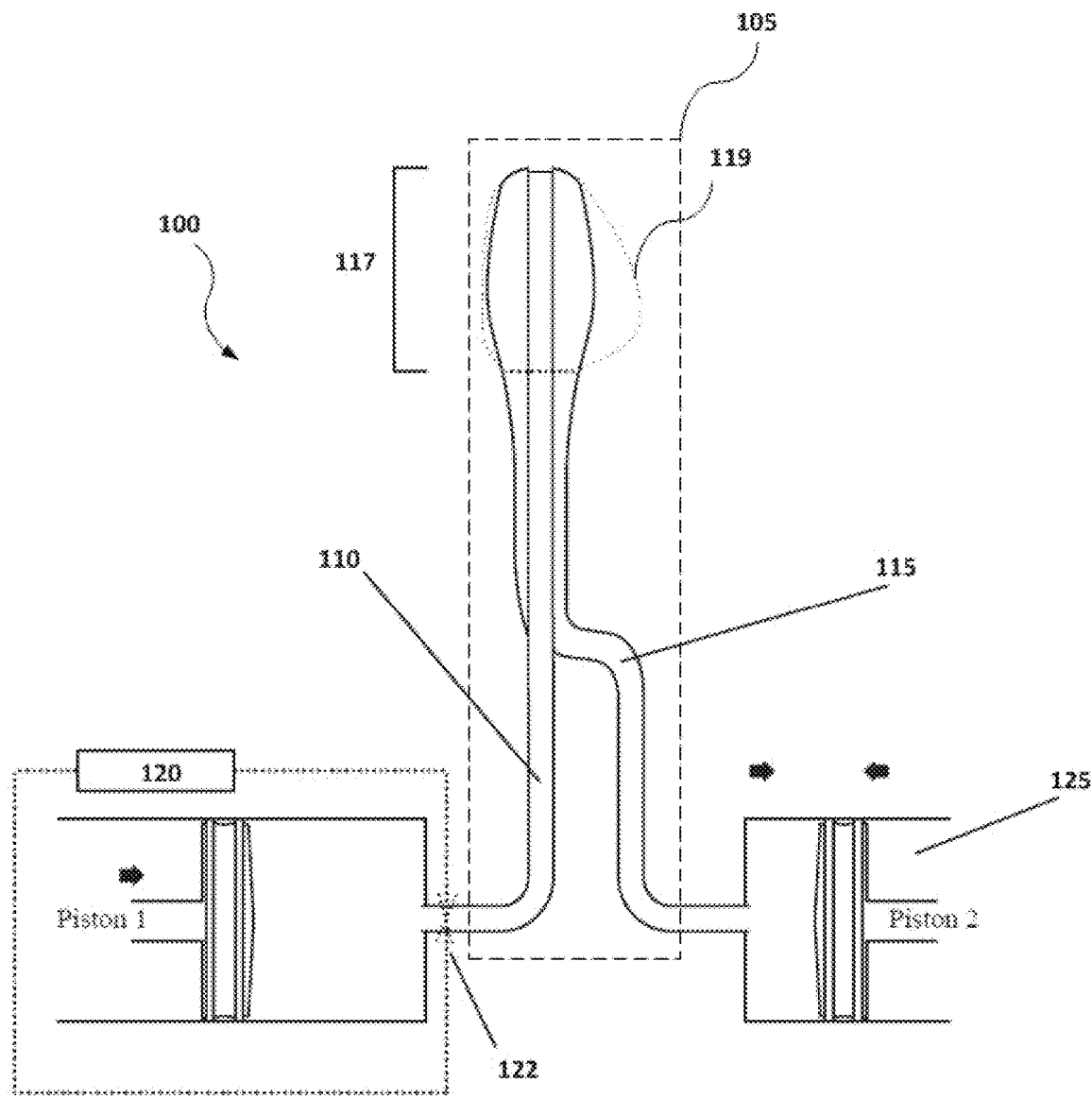
FIG. 1a is a schematic depiction of a device for providing intranasal liquid to nasal and/or paranasal cavities according to an example hereof.

FIG. 1a is a schematic depiction of a device for providing intranasal liquid to nasal and/or paranasal cavities and/or sinuses according to examples hereof. The device 100 may include two intranasal probes. In the example of FIG. 1a only one intranasal probe 105 is shown. Each intranasal probe may include a primary channel 110 and a secondary channel 115. A distal portion 117 of each of the probes may be configured to be inserted in a respective nostril, one distal portion for each of the nostrils, respectively. The primary channels 110 may be connected to a liquid dispenser 120. The liquid dispenser may include a pump or a dose dispensing cartridge. The primary channel may be open at one end of the probe and may be configured to provide liquid from the liquid dispenser 120 into the respective one of the nostrils in which that probe is inserted. The secondary channel may lead to a closed expandable portion 119 of the probe and may be used to provide fluid from fluid pump 125 to the expandable portion 119 of the probe. The expandable portion 119 may be an end portion of the secondary channel 115 and may be arranged around the distal end and/or opening of the primary channel 110.

Figure 1B:
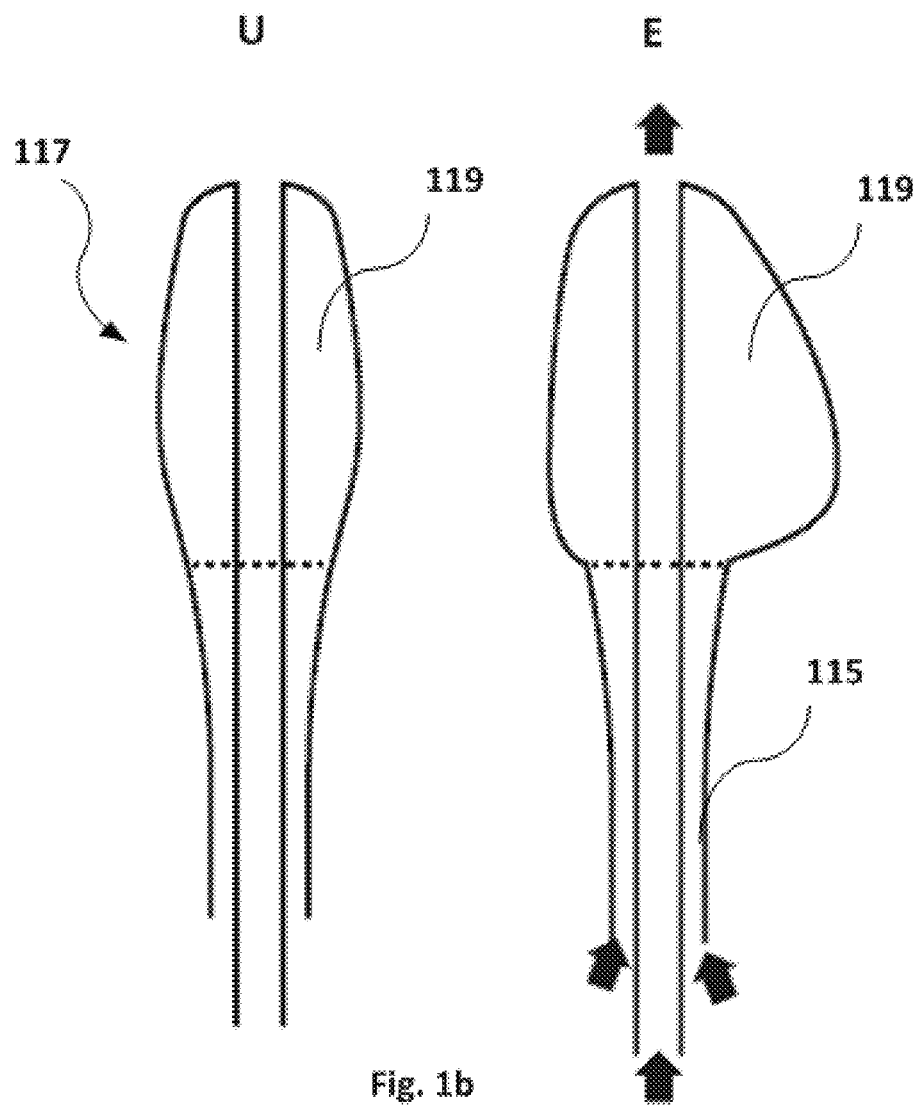
FIG. 1b is a schematic depiction of intranasal portions in respectively an unexpanded and an expanded state.
Figure 1C:
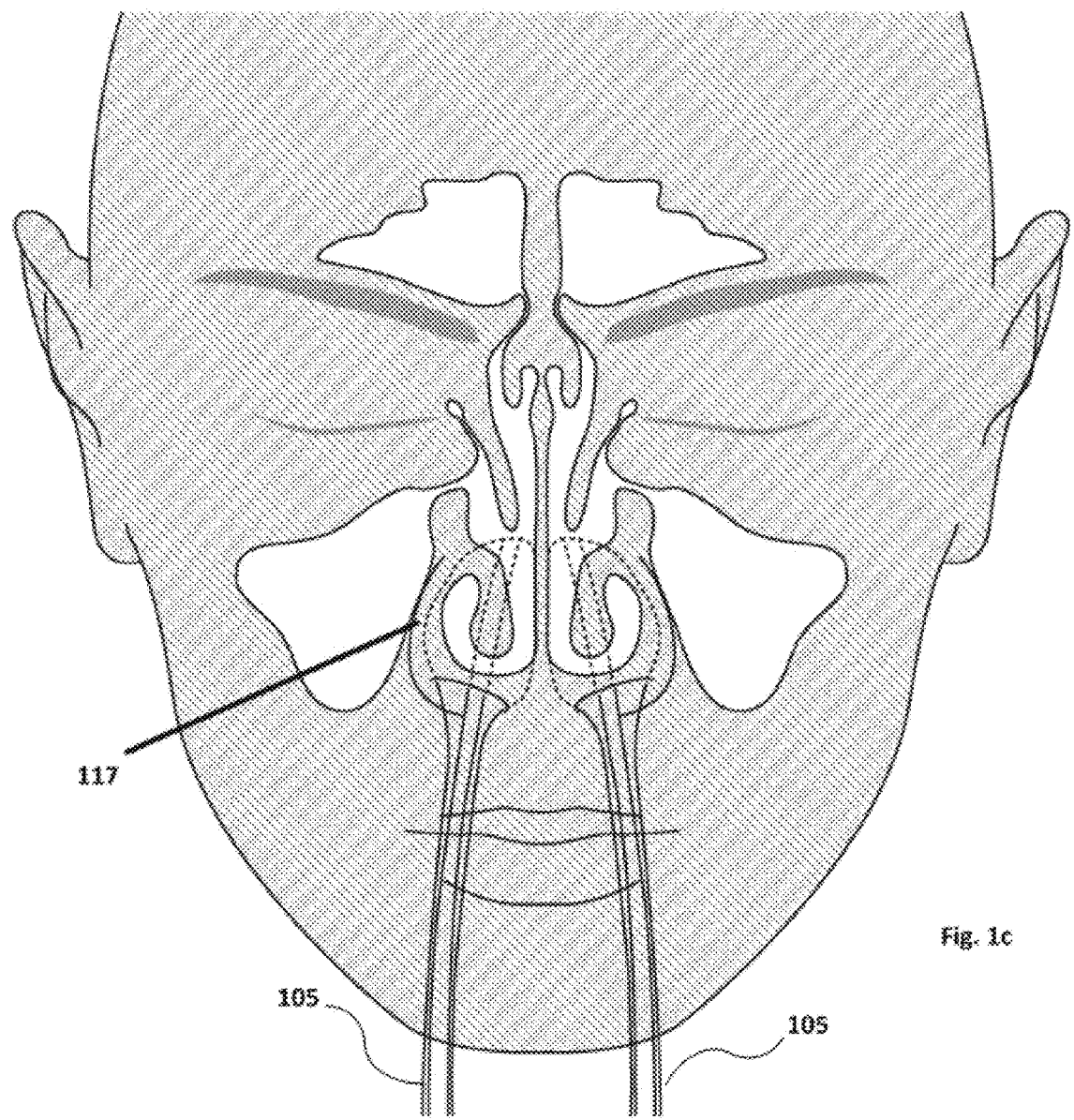
FIG. 1c is a schematic depiction of intranasal probes according to an example, applied to a user.

FIG. 1b is a schematic depiction of exemplar intranasal portions 117 in an unexpanded and an expanded state. In an unexpanded state (U) no fluid has been forced in the secondary channel 115 and the expandable portion 119 remains unexpanded. Then fluid (e.g., air or other gas or liquid) may be inserted (e.g. using a fluid pump) into and moved through the secondary channel 115 and into the expandable portion 119 so that the expandable portion 119 may then expand as shown in the expanded state (E). If the expandable portion has been inserted in a nostril then it may seal the nostril as it expands. The choice of fluid may depend on the material of the expandable portion. Air or other gas may be softer and more suitable for more gentle nostrils (e.g. for infants) whereas liquid may provide a more firm sealing and may be suitable for children or adults that may exhale with a higher force. FIG. 1c is a schematic depiction of intranasal probes 105 according to an example, applied to a user. The expandable portions of the distal portions 117 of two intranasal probes 105 are shown inserted in the nostrils of a user (e.g. a patient). As may be seen, the expansion of the expandable portions may expand the alar sidewalls of the nostrils. As will be explained later, this may assist in allowing for the opening or revealing of ducts leading to paranasal sinuses.

In a further non-limiting example hereof, a device hereof may include as shown in FIG. 1d, two relatively serial tubular central storehouses (1), of four departments (2) each, with, in some non-limiting examples, 2 or 3 or 4 cc of sea water in each department (e.g., infants-childrens-adults). In the outer end (3) each storehouse may have a movable pin (4) which with simple pressure with the fingers of the hands may provide to the pipe (5) the content of each department, e.g., namely 2-4 cc of water. Each stage of promotion of the pin may be guided by a trolling pin (6) that may be disposed to move on an interruptible driver (7). Each tubular storehouse may have or otherwise connect to a respective channel pipe (5) (a channel pipe (5) corresponding with intranasal probe 105 of FIGS. 1a, 1b and 1c) that ends in an edge with mouth or expandable portion (8) (a mouth (8) corresponding with expandable portion 119 of FIGS. 1a, 1b and 1c). Each channel pipe (5) may have a primary and a secondary channel defined therein. The central or primary channel (5a) (corresponding to primary channel 110 in the examples of FIGS. 1a and 1b) provides the water or other liquid of the tubular storehouse to the nose while the small or secondary channel (5b) (see FIGS. 1e and 1g, e.g.) (corresponding to the secondary channel 115 of FIGS. 1a and 1b) transfers the fluid, gas, water or otherwise from the small storehouse (9) disposed between the pipes to the periphery of the mouth (8) (mouth 8 being/corresponding to the expandable portion 119 of FIGS. 1a and 1b) which expands (see FIG. 1f, e.g.) for the elevation of the wing or alar sidewall of the nose and for sealed application for the facilitation of the water's entrance into the nasal cavity that fills the nasal cavity and the nasal conchas. The mouth or expandable portion (8) may have the anatomic shape of and/or matching the exit of the nasal cavity in order to achieve sealed application when the periphery of the mouth of the expandable portion (8) is expanding. It may have two points (10) out frontal and lower, so the mouth will be impacted in and based in the last upper-out and lower-out notch of the exit of the nasal cavity of the user.

Figure 1G:
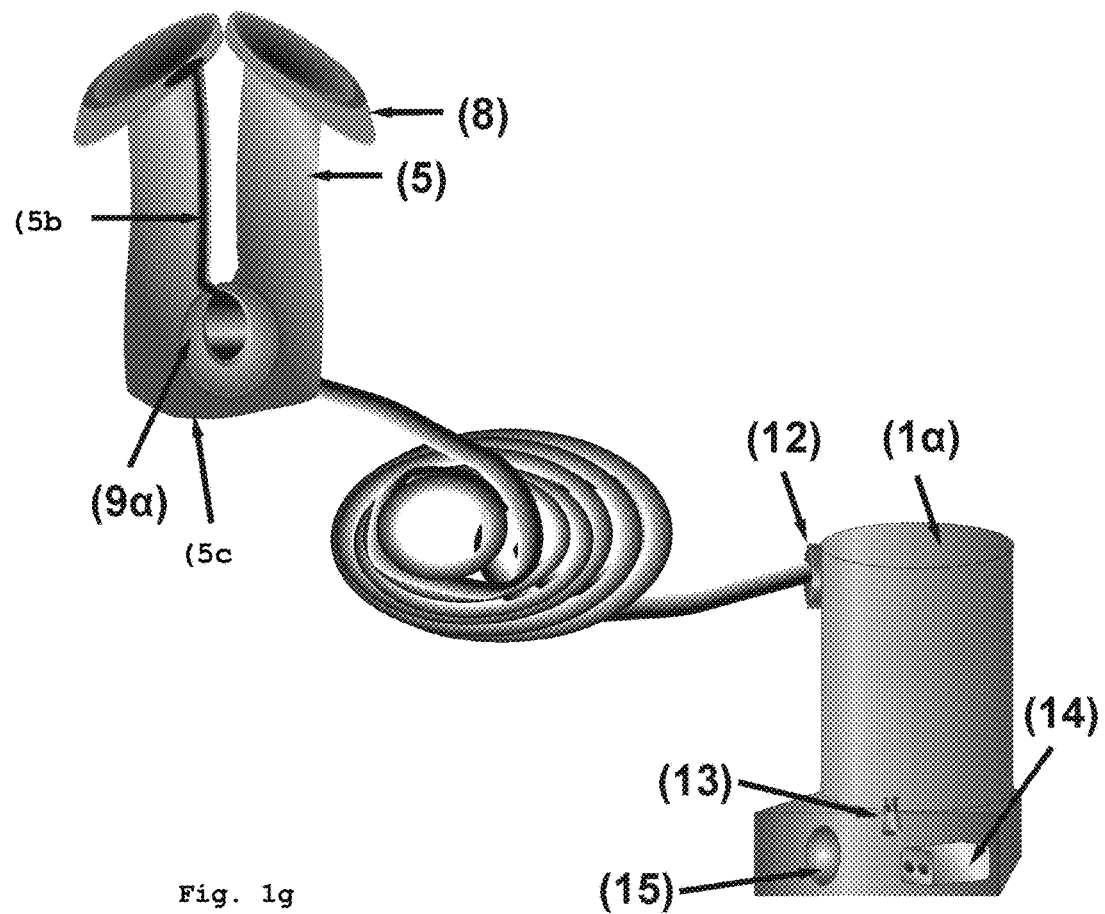
FIG. 1g shows another non-limiting example of a device hereof.

In a further non-limiting alternative form the device may have as shown in FIG. 1g two channel pipes (5) which by their mouths (8) are joined in one connecting pipe (5c). At the confluence of the channel pipes there may be a small storehouse (9a) that contains the fluid for expanding the periphery of the mouths or expandable portions (8). The connecting one pipe (5c) may end at and may be adapted to be in communication with an entrance (12) to/in a container (1a) of sufficient content of sea water or other useful fluid for therapeutic use herein. The container (1a) may bear in its base a pin (13) that may be moved by a thin mechanism supplied from a battery of 12 volt (14) and may be activated by simple pressure of a surface switch (15) providing movement of water or other therapeutic liquid therefrom to the nostrils (in some non-limiting examples, this may be 4, 6, and/or 8 cc of liquid). In a further non-limiting application as for example with this alternative device, the container (1a) may be of a multiple use or re-use type, for one person or for other users too, by the ability of refilling of the sea water or other therapeutic liquid. It may then be in some such examples that the connecting one pipe (5c) may be a personal consumable spare part attachable to the container 1a the part (5c) in some alternatives being of relatively fewer uses.

Figure 2:
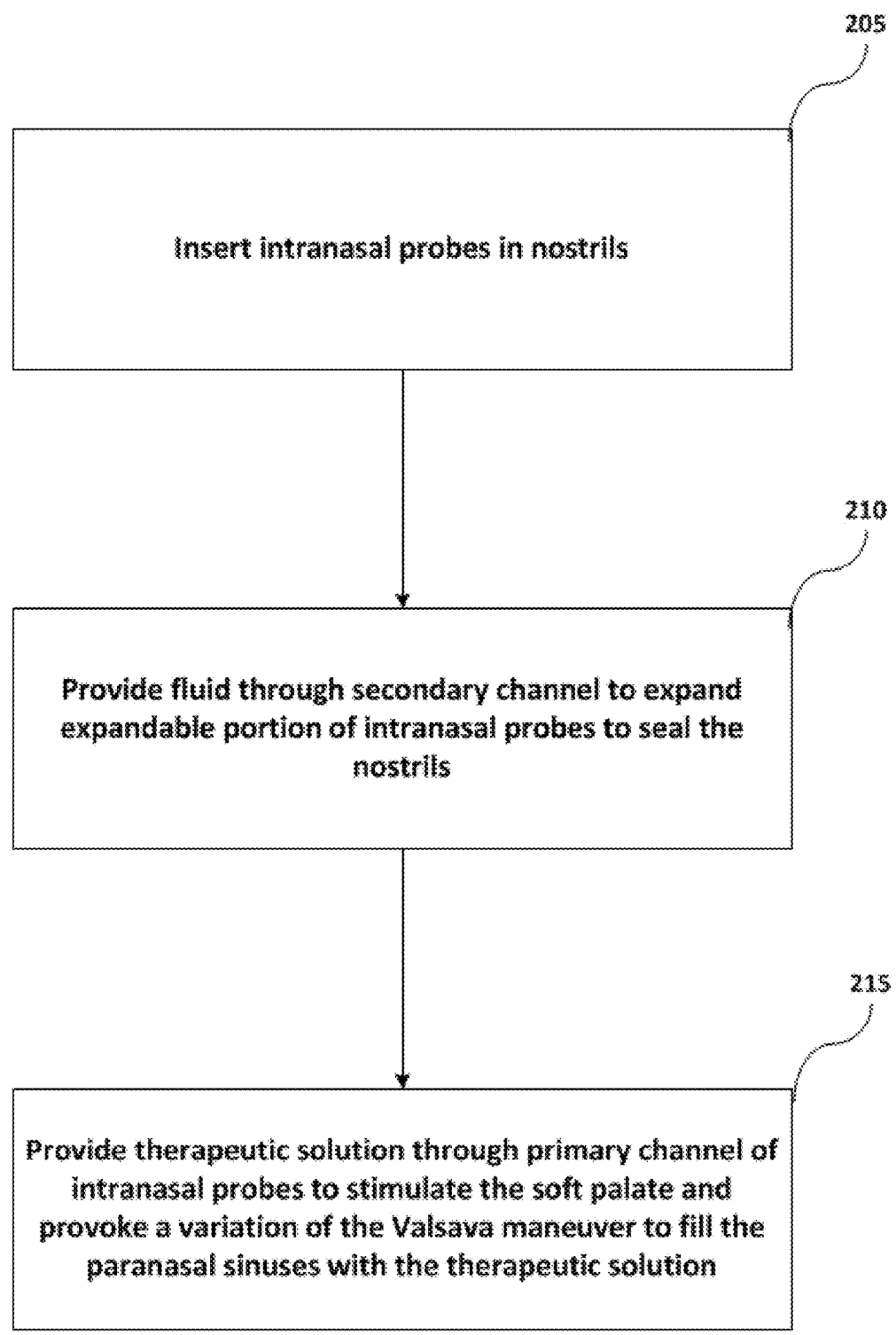
FIG. 2 is a flow chart of a method of providing intranasal liquid to nasal and/or paranasal cavities.

FIG. 2 is a flow chart of a method of providing intranasal liquid to nasal and/or paranasal cavities and/or sinuses. In a first step 205, the intranasal probes may be inserted in the nostrils. Each probe may include a primary channel and a secondary channel. Then, in a next step 210, an expandable portion of the intranasal probes may be expanded (as by using a fluid, such as liquid or air) to block and/or seal both nostrils, respectively, the blocking or sealing being achieved typically by expanding the expandable portion until the user is not able to inhale or exhale from the nose. The primary channel may be open and may be configured to provide liquid to the interior of the nostrils. The secondary channel may be closed and may be used to provide fluid to the expandable portion of the probe. The expandable portion may be an end portion of the secondary channel and may be arranged around the distal opening of the primary channel. With the bilateral obstruction of the nostrils the user may still breathe from the mouth (see e.g., Rf in FIG. 4b) while at the same time the alar sidewalls of the nostrils may be pushed outwards by the expandable portion of the secondary channel. This may result in an expansion of the nostrils, which may free the nasal conchae and reveal the orifices of the ducts leading to the sinuses. In a next step 215, there may be subsequent or simultaneous provision of therapeutic solution through the main or primary channels of the intranasal parts to both nostrils that are expanded. The provision may be performed with one dose or many smaller doses so that both nostrils may be filled equally, slowly and softly to avoid irritation of the user and so that the level of the therapeutic solution in the nostrils may be maintained substantially equal all the time.

Figure 3:
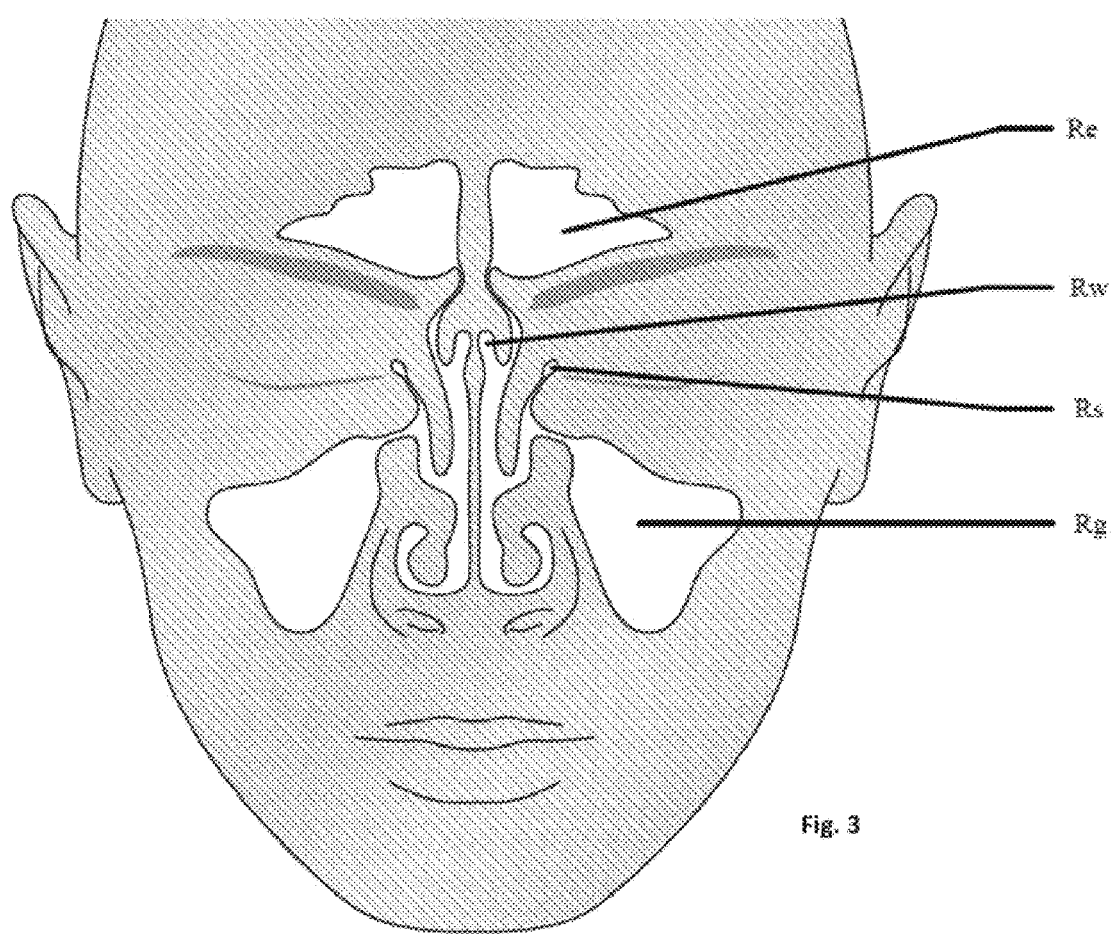
FIG. 3 schematically illustrates nasal and paranasal cavities.
Figure 4A:
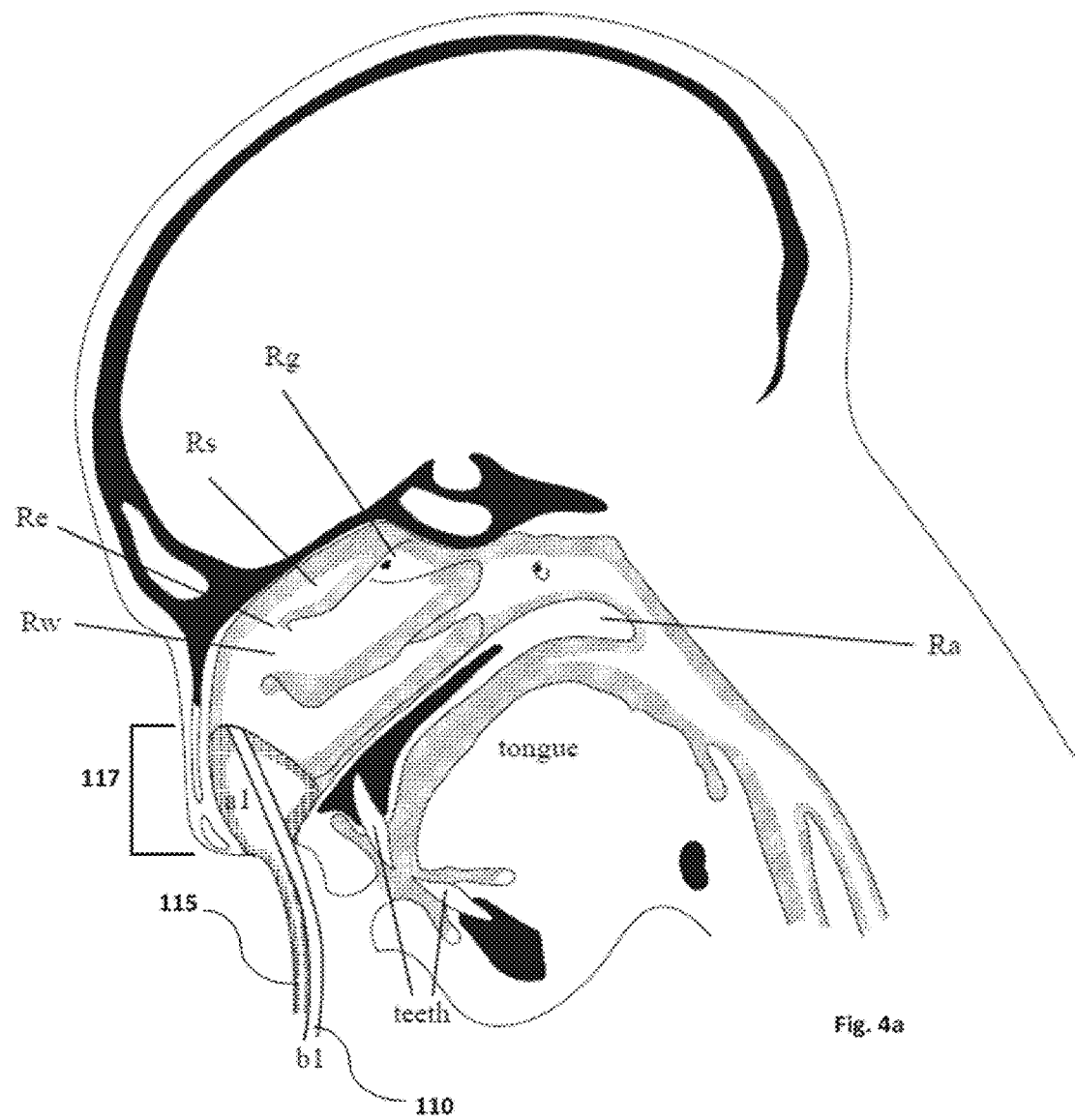
FIGS. 4a, 4b and 4c are section views of an inclined head during application of a method according to an example hereof.
Figure 4B:
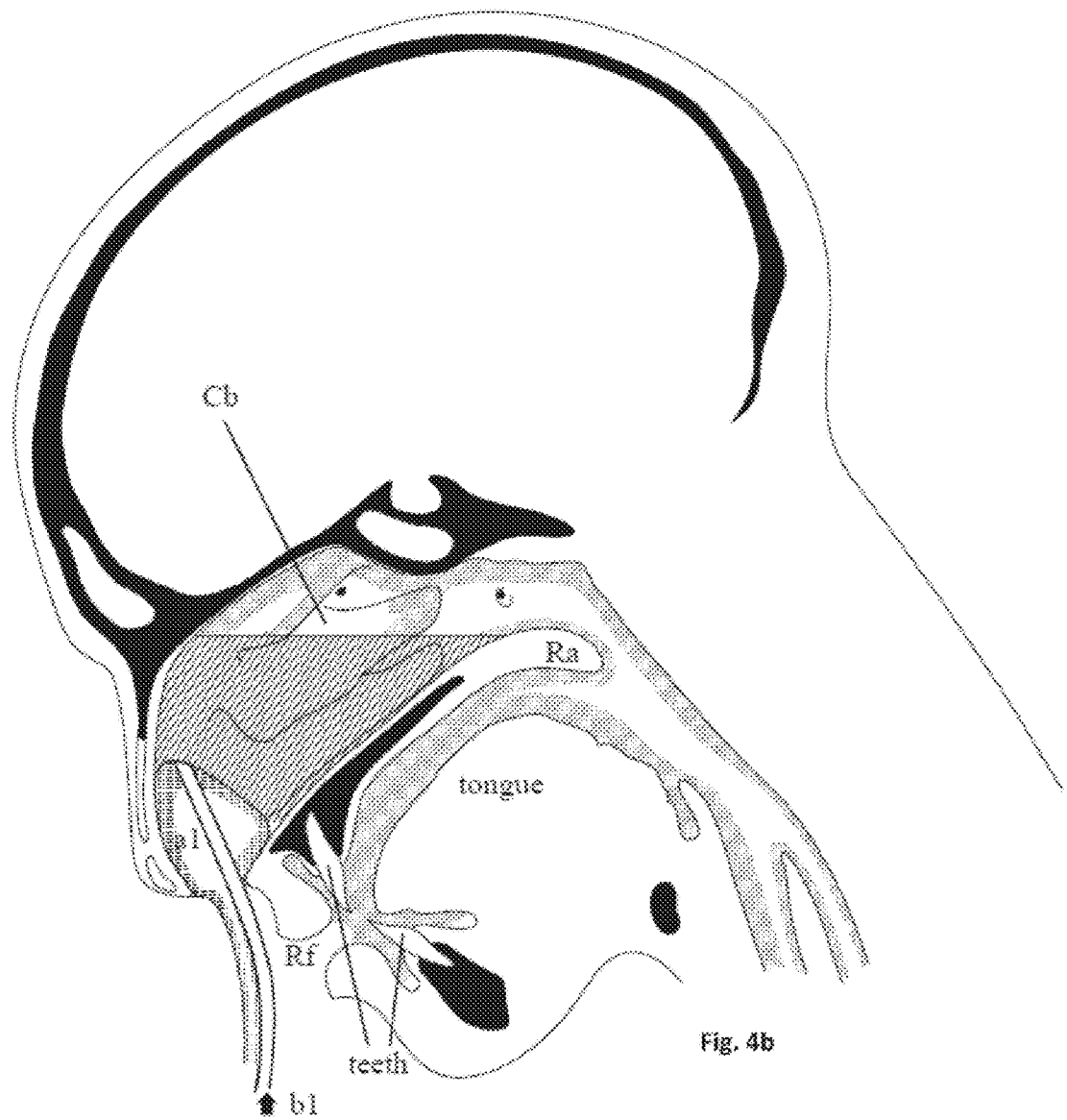
Figure 4C:
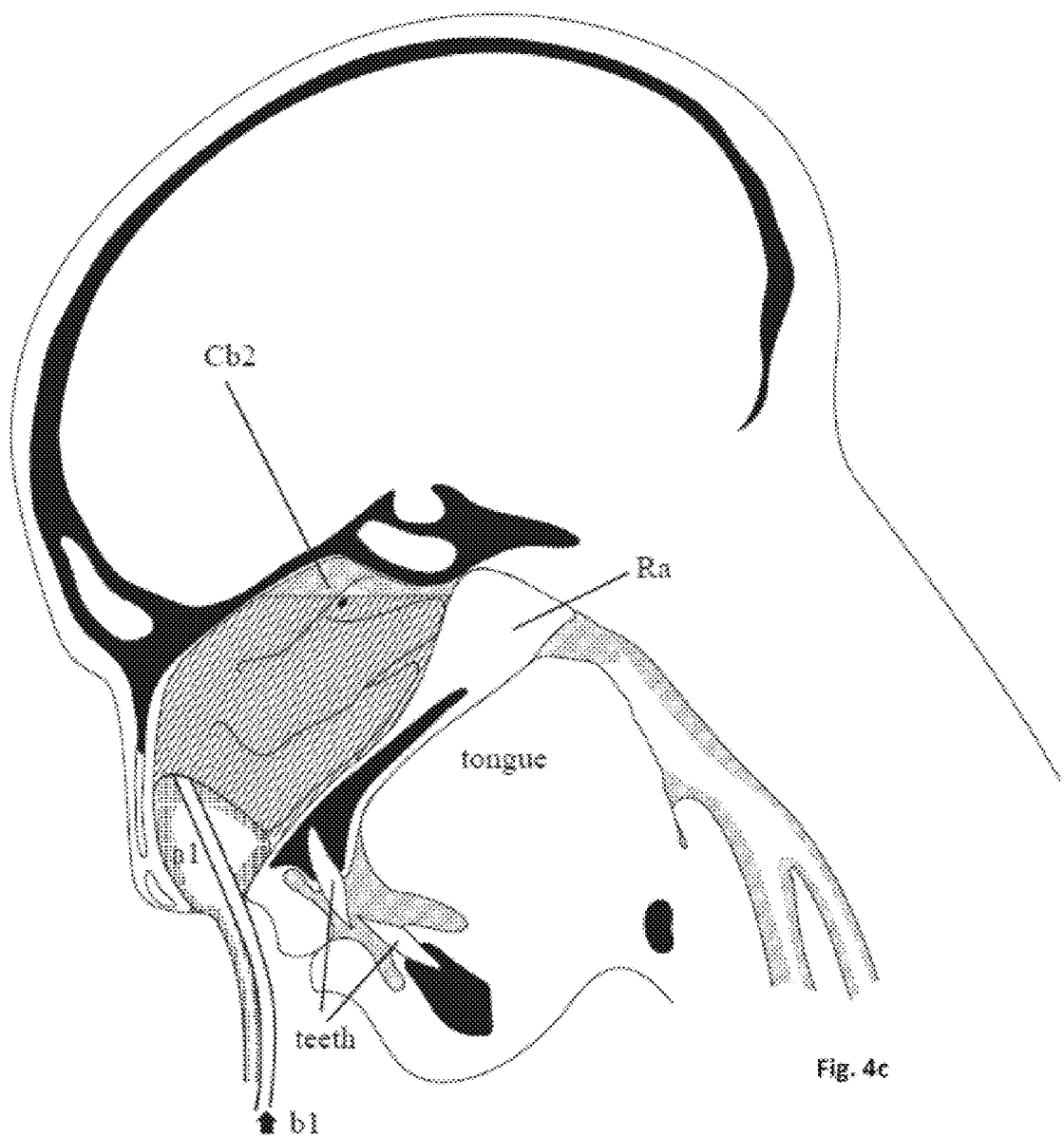

FIG. 3 schematically illustrates nasal and paranasal cavities (Rw, Re, Rs, Rg). FIG. 4a is a section view of an inclined head during the first step of an application of a method and/or device hereof. That is, the probes have been inserted into the nostrils but no liquid has yet been provided (fluid al in intranasal portion 117 via secondary channel 115 or solution b1 via secondary channel 110; see FIGS. 4a, 4b and 4c. Thus the soft palate Ra is in a relaxed unstimulated state. The head is in this implementation inclined to avoid passage of the liquid to the pharynx. FIG. 4b is a section view of an inclined head during a second step of an application of a method hereof. When the level of the provided solution reaches slowly to the plane of the soft palate (Cb), then the reflex of swallowing may be triggered. The reflex movement of swallowing may be complete due to the stimulation of the soft palate (Ra) by the intranasal therapeutic solution even though there is no bolus in the mouth for swallowing. To perform the swallowing reflex the soft palate may move upwards and frontwards. This is shown in FIG. 4c. The available space may be reduced and the level of the solution (Cb2) may be raised and cover the orifices of the ducts of the paranasal sinuses (Rw, Re, Rs, Rg (see FIG. 4a)). At the same time, the forward movement of the soft palate may push air towards the surface of the solution. Consequently, pressure may be exerted on the solution to push it towards the nostrils' openings. Because the nostrils' openings are blocked by the intranasal parts of the device, the solution may seek escape through the orifices of the ducts of the paranasal sinuses (Rw, Re, Rs, Rg (FIG. 4a)). In repetition of the swallowing movement the solution may find an escape route through the paranasal sinuses' ducts, while the device may slowly replenish the quantity of the solution so that the level of the solution remains at the level of the soft palate and maintains the stimulation of the soft palate. In some non-limiting implementations, the whole process, blocking of the nostrils, expansion of the alar sidewalls of the nostrils, revealing of the duct orifices of both nostrils with the expanding intranasal portions of the device, the simultaneous provision of solution to both nostrils, the stimulation or triggering of the automatic reflex of swallowing, the pressure to the surface of the solution from the forward moving air caused by the upward movement of the soft palate and the introduction of the solution to the paranasal sinuses—a process performed slowly and softly, at a pace acceptable by any user even by small children—provides a complete solution.

The perfectly tolerable use of the device may give the user the possibility to use the therapeutic process with ease, even when at work or while sitting on a couch (e.g. while watching TV), for as long as a user wants, providing an effective method. The friendliness of a prolonged therapeutic use provides the necessary time for the therapeutic solution to act during a necessary time to maximize the therapeutic result in the nasal and paranasal chambers. The time may range between five (5) and fifteen (15) minutes. However, in some cases even longer periods of half an hour may be beneficial so that the therapeutic effect of the liquid may take place.

The end result may provide an effective solution desired and long sought after by the medical community and users. It may be made possible by the combination of characteristics of the proposed devices and/or methods. That is, the devices may provide a complete sealing of the nostrils, in some implementations thus provoking the swallowing reflex when sufficient liquid is introduced in the nostrils. In some implementations in turn, the swallowing reflex may trigger a variation of the Valsalva maneuver. Without this succession of events there may be no pressure exerted to the surface of the solution and there may be no infusion of liquid in the ducts of the paranasal sinuses.

Furthermore, the way that the nasal cavities are sealed may not be a simple sealing but may produce some further effects: The expansion of the intranasal part of the device in the nostril may be disposed to push outwards the alar sidewalls of the nostrils which results in a widening of the nasal vestibule, and in some implementations thus freeing the nasal conchae and revealing the ducts of the paranasal sinuses which may facilitate the introduction of liquid to the paranasal sinuses.

Moreover, proper obstruction of both nostrils provided by the use of the proposed devices and/or methods, may allow the solution to remain in the nostrils and in the paranasal sinuses for as long as the user may wish, thereby providing the necessary time so that the therapeutic and/or cell-regenerative and/or healing properties of the medicine or of the saline (sea water) or of the extracts of aromatic plants to give results.

Therefore, the therapeutic result for the user or patient may depend on the proper application of the process that is provided by the proposed devices. It is also mentioned that an application of the solution to the nostrils may be performed in a soft and totally controllable manner and in small doses. This may in some applications be achieved by the small compartment that may provide solution under pressure which may be attached to the body of the device in such a way that with an application (pressure) only a small controlled quantity may be provided to both nostrils. The devices may be purely mechanical. The controlled and soft manner of providing the solution may create the conditions so that the devices and processes may be tolerable perfectly by the user and even by small children.

By the present developments a variation of the Valsalva exercise may successfully by achieved. A Valsalva movement increases the air pressure in the whole cavity of the upper respiratory tract when trying to expire with closed mouth and nostrils. A Valsalva exercise, as well as its variants, where a human swallows with his nose closed, is known to be applied for pressure equalization for airplane travelers, and this is why chewing gum is suggested during flight. When using a device hereof, the outer ducts of nostrils may be totally closed and the gentle application of the device pushes gently and without any pain its fluid contents, which are either sea water or an antibiotic or other therapeutic solution, or a solution with extracts of herbal plants towards the nasal cavities. When the cavities are filled, then the liquid moves backwards to the epipharynx and the swallowing reflex may be substantially automatically generated. For the swallowing to happen the soft palate is elevated and pushes the therapeutic liquid towards the nostrils exits. Since the nostrils are closed by the device, the content water is pressed and can find an escape route through the nasal concha and the foramens (apertures) of the excretory ducts of paranasal sinuses, gradually enters into the sinuses and a therapeutic result may be achieved.

Although only a number of examples have been disclosed herein, other alternatives, modifications, uses and/or equivalents hereof are possible. Furthermore, all possible combinations of the described examples are also covered. Thus, the scope of the present disclosure should not be limited by particular examples, but should be determined only by a fair reading of the claims that follow. If reference signs related to drawings are placed in parentheses in a claim, they are solely for attempting to increase the intelligibility of the claim, and shall not be construed as limiting the scope of the claim.

The invention claimed is:

1. A method of providing a liquid to paranasal cavities of a user, comprising:
introducing first and second probe portions respectively of a first probe and of a second probe, into a user's first and second nostril, respectively, wherein each probe comprises a primary channel and a secondary channel, each secondary channel comprising an expandable portion;
flowing a fluid to and through each secondary channel to expand each expandable portion of each secondary channel, and seal each nostril opening;
repeatedly flowing controlled doses of the liquid through the primary channels to the nasal cavity to stimulate a soft palate and provoke flowing of the liquid to paranasal sinuses, until a desired liquid quantity is present in the paranasal cavities.

2. A method according to claim 1, further comprising providing for one or more of the following:
the flowing of fluid to and through the secondary channels providing one or more of:
expanding alar sidewalls;
revealing conchae and
revealing ducts that lead to the paranasal cavities;
the flowing of one or more quantities of the liquid through the primary channels to the nasal cavity providing the liquid to be disposed to one or more of:
reach the soft palate; and
trigger a swallow reflex that one or more of:
raises the soft palate and
exerts pressure to the liquid,
whereby some of the liquid finds an escape route through the ducts and into the user's paranasal cavities.

3. A method according to claim 1, the desired liquid quantity being a therapeutically effective amount of the liquid in the paranasal cavities.

4. A method according to claim 1, wherein the liquid comprises saline.

5. A method according to claim 1, wherein the liquid comprises a medicinal liquid.

6. A method according to claim 1, wherein the liquid comprises extracts of herbal plants.

7. A method according to claim 1, wherein the liquid comprises an antibiotic solution.

8. A method according to claim 1, wherein the fluid is provided to the secondary channels by activating a fluid pump.

9. A method according to claim 8, wherein the fluid pump comprises an air pump and air is provided to the secondary channels by exerting pressure to a piston of the air pump.

10. A method according to claim 8, wherein the fluid pump comprises a liquid pump and the fluid is a liquid that is provided to the secondary channels by exerting pressure to a piston of the liquid pump.

11. A method according to claim 1, wherein the controlled doses of the liquid are provided to the nasal cavity by activating a primary liquid pump.

12. A method according to claim 11, further comprising attaching the primary liquid pump to the primary channels.

* * * * *